United States Patent [19]

Barone et al.

[11] Patent Number: 5,034,216
[45] Date of Patent: Jul. 23, 1991

[54] ANHYDROUS COSMETIC PRODUCT CONTAINING A PARTICULAR GEL PHASE

[75] Inventors: Salvatore J. Barone, Staten Island; Ralph A. Macchio, Monsey, both of N.Y.; Julio G. Russ, Germantown, Tenn.

[73] Assignee: Revlon, Inc., New York, N.Y.

[21] Appl. No.: 469,154

[22] Filed: Jan. 24, 1990

[51] Int. Cl.$^5$ .................. A61K 7/021; A61K 7/035
[52] U.S. Cl. ...................................... 424/63; 424/64; 424/69; 424/81
[58] Field of Search ............ 424/63, 64, 69, 78, 424/81; 514/944, 844, 845, 846, 847

[56] References Cited

U.S. PATENT DOCUMENTS

| | | | |
|---|---|---|---|
| 3,196,079 | 7/1965 | Blaustein | 424/63 |
| 3,574,822 | 4/1971 | Shepherd et al. | 424/47 |
| 3,909,280 | 9/1975 | Dench et al. | 106/271 |
| 4,167,433 | 9/1979 | Lakshmanan | 156/322 |
| 4,276,111 | 6/1981 | Karim et al. | 156/308.2 |
| 4,378,998 | 4/1983 | Korbanka et al. | 106/270 |
| 4,529,132 | 7/1985 | Hobes et al. | 241/1 |
| 4,574,082 | 3/1986 | Tietjen et al. | 424/63 |
| 4,673,571 | 6/1987 | Mahieu et al. | 424/70 |
| 4,678,664 | 7/1987 | Schmolka | 424/65 |
| 4,834,972 | 5/1989 | Chang | 424/78 |

FOREIGN PATENT DOCUMENTS 56-81512 7/1981 Japan.
61-257908 11/1986 Japan.

Primary Examiner—Thurman Page
Assistant Examiner—Susan S. Rucker
Attorney, Agent, or Firm—Julie Blackburn

[57] ABSTRACT

An anhydrous, three-phase powder-like cosmetic product comprising a) 10 to 60 weight % of a gel phase comprising ethylene/acrylate copolymer and an ester having the formula ROCOR, wherein R is an alcohol or fatty alcohol having a molecular weight of 60–400 and $R_1$ is a fatty acid having a molecular weight of 120–500;

b) 30 to 60 weight % of a powder phase comprising filler, color, preservative and substantially spherical silica particles having an average particle size of less than 15 microns; and c) 10 to 20 weight % of an oil phase comprising cosmetically acceptable alcohol esters of fatty acids.

9 Claims, No Drawings

ANHYDROUS COSMETIC PRODUCT CONTAINING A PARTICULAR GEL PHASE

TECHNICAL FIELD

This invention relates to pourable anhydrous gels, in stick, cake or cream form such as a cosmetic blush, lipstick, eyeshadow, mascara, eyeliner, and foundation. More particularly, this invention relates to a cosmetic gel formed from a copolymer of ethylene/acrylic acid and an ester of cosmetic oil.

PRIOR ART

Ethylene/acrylic acid copolymers have been used extensively to make polymer films, polishes, and waxes. The copolymers have been used in the past in cosmetics, but this use has been limited to a wax ingredient similar to carnauba wax, as shown in U.S. Pat. No. 4,574,082. The copolymers have not been used to form cosmetic gels.

U.S. Pat. No. 4,837,011 discloses spherical silica having a particle size of 6-20 microns in a cosmetic powder. Published Japanese Patent Application 95395/1985 filed May 7, 1985 discloses spherical cosmetic powders of organic and inorganic materials, including silica, coated with a polymer, such as polyethylene. However, these references do not show a cosmetic made from ethylene/acrylic acid copolymers.

Previous anhydrous pourable gel based cosmetics have been limited in their application and versatility. The gels have difficulty dispersing the powder ingredients (fillers, pigments and color) uniformly throughout the gel.

It is therefore highly desirable to formulate a powder-like anhydrous cosmetic gel compatible with conventional cosmetic powder ingredients, which is exceedingly smooth, and which can be applied like a powder by the use of a brush, fingers or an applicator.

SUMMARY OF THE INVENTION

It has now been found that the above and other objects of this invention can be achieved by formulating a three-phase anhydrous cosmetic product comprising a gel phase of ethylene/acrylic acid copolymer and a cosmetically acceptable ester, a powder phase containing filler, color, preservative and microfine spherical particles of silica as an essential component, said silica having an average particle size of 1-15 microns, and an oil phase containing cosmetically acceptable esters, oils, and fragrance. The cosmetic gel of this invention is highly stable, non-reactive and compatible with cosmetic powders, oils and waxes. It has unusual swelling properties which permit up to 60 weight % of solid ingredients in the powder phase to be absorbed by the gel.

At least 10 weight % of the particles in the powder phase are coated with a polymer, such as polyethylene. The coating being present at a 1-3 weight % of the coated material. The silica is at least 10 weight % of the total composition.

DETAILED DESCRIPTION OF THE INVENTION

The three-phase system employs 10-60 weight % of the gel phase of ethylene/acrylic acid copolymer; 20-60 weight % of the powder phase, and 10-20 weight % of the oil phase.

As indicated the copolymer which acts as gelling agent for the gel phase is an ethylene/acrylic acid copolymer. The ethylene/acrylic acid copolymer is mainly comprised of ethylene chains with small amounts of functional groups attached. The copolymers have a molecular weight of 2000-3000 with the following properties:

| Drop Point | | Hardness | Density | Brookfield Viscosity cps | Acid No. mg |
|---|---|---|---|---|---|
| °C. | F.° | dmm | g/cc | at 140° C. | KOH/g |
| 108 | 226 | 2.0 | 0.93 | 500 | 40 |
| 102 | 216 | 4.0 | 0.93 | 650 | 75 |
| 92 | 198 | 11.5 | 0.93 | 650 | 120 |

The cosmetic ester is an alcohol ester of a fatty acid having the formula ROCOR, wherein R is an alcohol having a molecular weight of 60-400, and $R_1$ is an acid having a molecular weight of 120-500.

The gel phase of this invention is formed by simply mixing the 1-6 weight % of gelling agent with the oil phase containing 20-40 weight % of the desired ester at 80°-90° C. to form a homogeneous gel phase solution. The ester is one normally used in the oil phase of a cosmetic product. Preferred is octyl stearate, or isopropyl isostearate, but other similar esters can be used. These include glycerol esters, $C_3$-$C_{22}$ alcohol esters of $C_3$-$C_{22}$ fatty acids, and $C_{12}$-$C_{22}$ fatty alcohols. In addition to the ester which interacts with the gelling agent to form the essential gel phase of this invention, the oil phase may contain up to 20 weight % of additional cosmetically acceptable esters, oils, waxes, fragrances, emollients and the like, depending on the particular end product desired.

The powder phase of this invention employs substantially spherical particles of silica as an essential filler ingredient. The silica is at least 10 weight % of the total cosmetic composition. The silica spheres have an average particle size of less than 15 microns, with an average particle size of 2-5 microns being preferred. The microspheres of silica help to give a silky, smooth feel to the final product. Additionally, smoothness is enhanced by treating the silica with a polymer coating of polyethylene or other similar polymer. Smoothness is enhanced by coating the silica with polyethylene. At least 10 weight % of the total composition should be treated or coated with the polyethylene at a level of 1-3 weight %, preferably 1-2 weight % of the coated material. Alternatively, other fillers, besides or instead of the silica, such as the pigments and colors used in the powder phase may be treated with the polymeric coating. All fillers, pigments, and colors added should have a particle size below 15 microns, and preferably an average particle size of 2-5 microns.

While optional, it is preferred to add 5-15 weight % of microspheres of a polymeric material, such as polymethylmethacrylate (PMMA), nylon, or polyethylene, to the silica in the powder phase. These microspheres also have a particle size below 15 microns, and further improve the smooth feel of the product. PMMA is most preferred, and a titanated form (PMMA isopropyl isostearyl titanate) or untitanated form (PMMA) can be used.

DESCRIPTION OF THE PREFERRED EMBODIMENTS

The generic cosmetic gel of this invention comprises the following parts by weight:

| | |
|---|---|
| Ethylene/acrylate copolymer | 1–6 |
| Isopropyl isostearate | 10–50 |
| Silica (spherical) | 1–30 |
| Treated pigments and colors | 1–25 |
| Oils, esters & fragrances | 10–20 |

The preferred gel phase is formed by reacting the copolymer with isopropyl isostearate as the preferred ester. The oil phase may include any conventional oil, ester, fragrance or perfume used in cosmetic formulations. These include peg-4-diheptanoate, octyl stearate, isostearyl neopentanoate, sorbitan sesquioleate, trilaurin, geranium extract/dipropylene glycol, etc. The powder phase, aside from silica, as the essential powder, preferably includes PMMA in titanated or untitanated form, treated pigments and treated colors. The treated pigments are talc, titanium dioxide, mica, kaolin or similar equivalents coated with polyethylene. The treated colors are iron oxide, zinc oxide or similar equivalents coated with polyethylene. The powder phase also contains conventional preservatives. These are propyl paraben, phenoxy ethanol, butyl paraben, benzoic acid, methyl paraben, and imidazolidinyl urea. These preservatives are used at a level of 0.2–2.0 weight %, but a preferable range is 0.2–1.5 weight %. Antioxidants, such as BHA, are used at a level of 0.01–0.20.

To make the cosmetic gels of this invention, one stirs the copolymers and ester together to form the gel phase. The oil phase is then added until a uniform mixture is achieved. After the oil phase and gel phase have been combined the powder phase (treated fillers, treated pigments, treated colors and preservatives) are then added to the liquid mixture and dispersed using high shear equipment until a homogeneous dispersion is obtained. The dispersion is then heated to a point above the melting temperature of any wax material which is to be added (usually 70°–90°). The mixture is then poured hot (70°–90° C.) into jars, sticks, pencils and the like.

This invention will now be described by reference to the following examples which are illustrative. The above procedure was used in each example for preparing the final product.

EXAMPLE 1

Blusher

| | |
|---|---|
| Ethylene/acrylate copolymer | 3.84 |
| Isopropyl isostearate | 37.25 |
| Peg-4-diheptanoate | 4.20 |
| Octyl stearate | 4.20 |
| Isostearyl neopentanoate | 6.10 |
| Sorbitan sesquioleate | 0.50 |
| Trilaurin | 2.20 |
| Geranium Extract/dipropylene glycol | 0.10 |
| BHA | 0.10 |
| Preservatives | 1.65 |
| Titanium dioxide/polyethylene | 2.00 |
| Red iron oxide/polyethylene | 1.20 |
| Yellow iron oxide/polyethylene | 1.15 |
| Black iron oxide/polyethylene | 0.25 |
| Red 6 barium lake | 0.05 |
| Polymethyl methacrylate | 11.00 |
| Silica | 15.00 |
| Mica/polyethylene | 9.20 |
| Dimethicone | 0.01 |
| | 100.00 |

EXAMPLE 2

Foundation

| | |
|---|---|
| Ethylene/acrylate copolymer | 3.64 |
| Isopropyl isostearate | 37.25 |
| Peg-4-diheptanoate | 4.20 |
| Octyl stearate | 4.20 |
| Isostearyl neopentanoate | 6.10 |
| Sorbitan sesquioleate | 0.50 |
| Trilaurin | 2.20 |
| Geranium extract/dipropylene glycol | 0.10 |
| BHA | 0.10 |
| Preservatives | 1.65 |
| Titanium dioxide/polyethylene | 6.03 |
| Red iron oxide/polyethylene | 0.56 |
| Yellow iron oxide/polyethylene | 1.58 |
| Black iron oxide/polyethylene | 0.19 |
| Polymethyl methacrylate/titanate | 5.03 |
| Silica | 17.08 |
| Mica/polyethylene | 9.39 |
| Dimethicone | 0.01 |
| | 100.00 |

EXAMPLE 3

Eye Shadow

| | |
|---|---|
| Ethylene/acrylate copolymer | 3.84 |
| Isopropyl isostearate | 37.25 |
| Peg-4-diheptanoate | 4.20 |
| Octyl stearate | 4.20 |
| Isostearyl neopentanoate | 6.10 |
| Sorbitan sesquioleate | 0.50 |
| Trilaurin | 2.20 |
| Geranium extract/dipropylene glycol | 0.10 |
| BHA | 0.10 |
| Preservatives | 1.65 |
| Titanium dioxide | 2.20 |
| Yellow iron oxide/polyethylene | 1.00 |
| Titanium dioxide/mica/iron oxide | 1.65 |
| Polymethyl methacrylate | 11.00 |
| Silica | 15.00 |
| Mica/polyethylene | 9.20 |
| Dimethicone | 0.01 |
| | 100.00 |

EXAMPLE 4

Lipstick

| | |
|---|---|
| Ethylene/acrylate copolymer | 3.46 |
| Isopropyl isostearate | 33.53 |
| Peg-4-diheptanoate | 3.78 |
| Octyl stearate | 3.78 |
| Isostearyl neopentanoate | 5.49 |
| Sorbitan sesquioleate | 0.45 |
| Trilaurin | 1.98 |
| Geranium extract/dipropylene glycol | 0.09 |
| Ceresin wax | 10.00 |
| BHA | 0.09 |
| Preservatives | 1.48 |
| Titanium dioxide/polyethylene | 1.80 |
| Red No. 7 | 1.40 |
| Yellow No. 5 | 0.16 |
| Polymethyl methacrylate | 9.90 |
| Silica | 13.50 |
| Mica/polyethylene | 8.14 |
| Dimethicone | 0.01 |

-continued

|  | |
|---|---|
|  | 100.00 |

EXAMPLE 5

Pencil

| | |
|---|---|
| Ethylene/acrylate copolymer | 3.46 |
| Isopropyl isostearate | 33.53 |
| Peg-4-diheptanoate | 3.78 |
| Octyl stearate | 3.78 |
| Isostearyl neopentanoate | 5.49 |
| Sorbitan sesquioleate | 0.45 |
| Trilaurin | 1.98 |
| Geranium extract/dipropylene glycol | 0.09 |
| Ceresin wax | 10.00 |
| BHA | 0.09 |
| Preservatives | 1.48 |
| Titanium dioxide/polyethylene | 1.80 |
| Black iron oxide | 3.67 |
| Titanium dioxide | 0.96 |
| Polymethyl methacrylate | 9.90 |
| Silica | 13.50 |
| Mica/polyethylene | 6.00 |
| Dimethicone | 0.01 |
| | 100.00 |

While this invention has been described by specific examples, it is apparent that various changes and modifications may be made without departing from the spirit and scope thereof. Therefore, the invention is not to be limited except as defined in the following claims.

What is claimed is:

1. An anhydrous, three-phase powder-like cosmetic product comprising
   a) 10 to 60 weight % of a gel phase comprising ethylene/acrylate copolymer and an ester having the formula $ROCOR_1$ wherein R is an alcohol or fatty alcohol having a molecular weight of 60–400 and $R_1$ is a fatty acid having a molecular weight of 120–500;
   b) 20 to 60 weight % of a powder phase comprising filler, color, preservative and at least 10 weight % of substantially spherical silica particles having an average particle size of less than 15 microns; and
   c) 10 to 20 weight % of an oil phase comprising cosmetically acceptable alcohol esters of fatty acids.

2. The composition of claim 1 wherein the ester in the gel phase is isopropyl isostearate.

3. The composition of claim 1 wherein the filler in the powder phase comprises 5–15 weight % of polymethyl methacrylate.

4. The composition of claim 1 wherein the filler in the powder phase comprises 2–30 weight % mica, titanium dioxide, and color.

5. The composition of claim 1 wherein the silica in the powder phase has an average particle size of 2–5 microns.

6. The composition of claim 1 wherein at least 10 weight % of the particles in the powder phase are coated with polyethylene.

7. The composition of claim 3 wherein the polymethyl methacrylate is polymethyl methacrylate isopropyl isostearoyl titanate.

8. The composition of claim 4 wherein the mica, titanium dioxide, and color are coated with polyethylene.

9. The composition of claim 6 wherein the particles coated with polyethylene are silica.

* * * * *